US008556823B2

(12) United States Patent
Koest et al.

(10) Patent No.: US 8,556,823 B2
(45) Date of Patent: Oct. 15, 2013

(54) OPHTHALMOLOGICAL ANALYSIS METHOD AND ANALYSIS SYSTEM

(75) Inventors: Gert Koest, Hannover (DE); Andreas Steinmueller, Wettenberg (DE)

(73) Assignee: Oculus Optikgeraete GmbH, Wetzlar-Dutenhofen (DE)

(*) Notice: Subject to any disclaimer, the term of this patent is extended or adjusted under 35 U.S.C. 154(b) by 77 days.

(21) Appl. No.: 13/165,541

(22) Filed: Jun. 21, 2011

(65) Prior Publication Data
US 2011/0319740 A1 Dec. 29, 2011

(30) Foreign Application Priority Data

| Jun. 21, 2010 | (EP) | 10166681 |
| Oct. 28, 2010 | (DE) | 10 2010 049 633 |
| Oct. 28, 2010 | (DE) | 10 2010 049 634 |
| May 31, 2011 | (EP) | 11168232 |
| May 31, 2011 | (EP) | 11168234 |
| May 31, 2011 | (EP) | 11168235 |

(51) Int. Cl.
*A61B 3/10* (2006.01)
*A61B 3/107* (2006.01)
*A61B 3/113* (2006.01)
*A61B 3/14* (2006.01)
*A61B 3/16* (2006.01)

(52) U.S. Cl.
USPC ........... 600/558; 351/200; 351/212; 351/246; 600/398; 600/401; 600/405; 600/587

(58) Field of Classification Search
USPC .......... 351/200, 246, 212; 600/398, 401, 405, 600/558, 587
See application file for complete search history.

(56) References Cited

U.S. PATENT DOCUMENTS 3,406,681 A 10/1968 Zandman
5,614,966 A * 3/1997 Iijima et al. .................. 351/208
(Continued)

FOREIGN PATENT DOCUMENTS

CN 101653354 A 2/2010
DE 10 2006 039 893 A1 3/2007
(Continued)

OTHER PUBLICATIONS

European Search Report issued in corresponding application No. EP 11168234.0, completed on Oct. 10, 2011 and mailed Oct. 19, 2011.
(Continued)

*Primary Examiner* — Sean Dougherty
(74) *Attorney, Agent, or Firm* — Griffin & Szipl, P.C.

(57) ABSTRACT

The invention relates to an ophthalmological analysis method for measuring an intraocular pressure in an eye with an analysis system consisting of an actuating device, wherein the actuating device causes a puff of air to be applied to the eye in such manner that the cornea is deformed, an observation system with which the deformation of the cornea is observed and recorded, wherein sectional images of the cornea when it is deformed and not deformed are created with the observation device, and an analysis device with which the intraocular pressure is derived from the sectional images of the cornea, wherein a structural characteristic and/or material characteristic of the cornea is derived from the sectional images of the cornea in the analysis device, wherein a stress of the cornea is derived as a structural characteristic and/or material characteristic, wherein stresses in the corneal material are rendered visible.

20 Claims, 4 Drawing Sheets

(56) References Cited

U.S. PATENT DOCUMENTS

Figure 1:
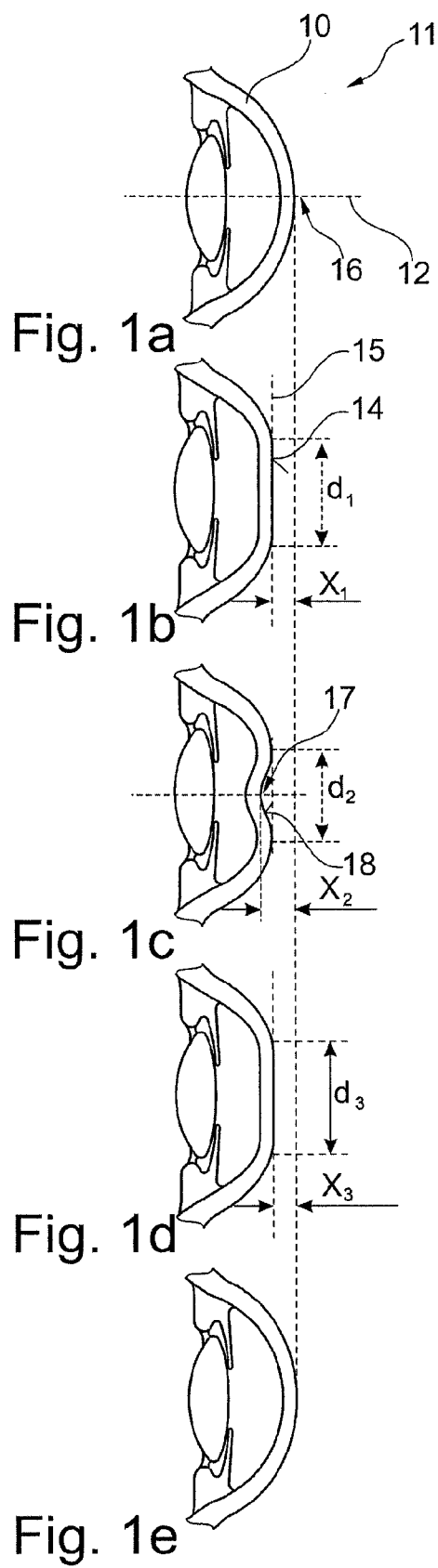

| | | | |
|---|---|---|---|
| 5,822,035 A | 10/1998 | Bille | |
| 6,120,444 A | 9/2000 | Miyakawa et al. | |
| 7,153,266 B2* | 12/2006 | Uchida | 600/399 |
| 7,235,051 B2* | 6/2007 | Iwanaga | 600/401 |
| 7,364,298 B2* | 4/2008 | Hayashi et al. | 351/212 |
| 7,481,767 B2 | 1/2009 | Luce | |
| 7,909,765 B2 | 3/2011 | Luce | |
| 8,152,302 B2 | 4/2012 | Bille | |
| 2004/0046936 A1* | 3/2004 | Iwanaga | 351/212 |
| 2005/0030473 A1 | 2/2005 | Fahrenkrug et al. | |
| 2006/0241367 A1 | 10/2006 | Koest | |
| 2007/0055122 A1 | 3/2007 | Luce | |
| 2007/0097317 A1* | 5/2007 | Hayashi et al. | 351/200 |
| 2007/0121120 A1 | 5/2007 | Schachar | |
| 2007/0146636 A1* | 6/2007 | Ishikura | 351/221 |
| 2009/0036761 A1* | 2/2009 | Abreu | 600/318 |
| 2009/0093698 A1 | 4/2009 | Luce | |
| 2009/0216106 A1* | 8/2009 | Takii | 600/401 |
| 2011/0032480 A1* | 2/2011 | Rathjen | 351/206 |
| 2011/0222021 A1* | 9/2011 | Rathjen | 351/214 |
| 2012/0162605 A1* | 6/2012 | Koest | 351/221 |
| 2012/0218518 A1* | 8/2012 | Wada | 351/208 |
| 2012/0310073 A1* | 12/2012 | Koest et al. | 600/401 |

FOREIGN PATENT DOCUMENTS

| | | | |
|---|---|---|---|
| EP | 1 692 998 A1 | 8/2006 | |
| JP | H10 213483 A | 8/1998 | |
| JP | H10 309265 A | 11/1998 | |
| JP | 2000254101 A | 9/2000 | |
| JP | 2002-263069 A | 9/2002 | |
| JP | 2006231052 A | 9/2006 | |
| JP | 2007121174 A | 5/2007 | |
| JP | 2008011878 A | 1/2008 | |
| JP | 2008298767 | 12/2008 | |
| JP | 2009273715 A | 11/2009 | |
| JP | 2012519553 A | 8/2012 | |
| WO | 2007 056292 A3 | 5/2007 | |

OTHER PUBLICATIONS

Kaneko, Makoto et al., "Dynamic Sensing of Human Eye," Proceedings of the 2005 IEEE, International Conference on Robotics and Automation, Apr. 2005, pp. 2871-2876.

Kempf, Roland et al., "Understanding eye deformation in non-contact tonometry," Proceedings of the 28th IEEE, EMBS Annual International Conference, Aug. 2006, pp. 5428-5431.

English Translation of Korean Intellectual Property Office Notice of Rejection issued in parallel application No. 10-2011-0060130, mailed on Dec. 7, 2012.

Actuator, McGraw-Hill Dictionary of Scientific and Technical Terms, (6th ed.) 2003, p. 32.

Office Action in parallel Australian application. Application No. 2011202972, issued Jan. 21, 2013.

English Translation of a Japanese Office Action in a parallel application. Application No. 2011-136552, issued Feb. 1, 2013.

Chinese Office Action in Chinese parallel case No. 2011/10169734.9 dated May 6, 2013 and received Jun. 14, 2013 w/English Translation.

English Translation of a Japanese Office Action relating to a parallel Japanese action (2011 136548), drafted Jun. 5, 2013 and received Jun. 10, 2013.

English Translation of a Chinese Office Action with search report relating to a parallel Chinese action (2011 10169822.9) issued May 30, 2013.

"An Experimental Observation of Photoelastic Stress of Human Joint at Different Flex Angle," Journal of Applied Biomechanics, vol. 13, No. 4, Dec. 1998, with English Abstract.

"Photoelastic technology is used to measure stress," Electronic Test, Jan. 2009, No. 2; Feng Xiaoqin, Song Wen'ai, Ma Jinhong, (North University of China, Key laboratory of instrumentation science and dynamic measurement, Taiyuan 030051 China), with English Abstract.

* cited by examiner

OPHTHALMOLOGICAL ANALYSIS METHOD AND ANALYSIS SYSTEM

This is a U.S. patent application which claims priority from European Patent Application No. 10166681.6, filed Jun. 21, 2010, German patent Application No. 10 2010 049 634.0, filed Oct. 28, 2010, German patent Application No. 10 2010 049 633.2, filed Oct. 28, 2010, European Patent Application No. 11168235.7, filed May 31, 2011, European Patent Application No. 11168232.4, filed May 31, 2011, and European Patent Application No. 11168234.0, filed May 31, 2011. The entire disclosures of the above patent applications are hereby incorporated by references.

FIELD OF THE INVENTION

The invention relates to an ophthalmological analysis method for measuring an intraocular pressure in an eye with an analysis system, including an analysis system of such kind consisting of an actuating device, with which an eye cornea is deformed in contactless manner, wherein a puff of air is applied to the eye via the actuating device to deform the cornea, an observation system that is used to observe and record the corneal deformation, wherein sectional images of the cornea with and without deformation are recorded with the observation system, and an analysis device that is used to derive the intraocular pressure from the sectional images of the cornea, wherein a structural characteristic and/or a material characteristic of the cornea is derived from the sectional images in the analysis device.

BACKGROUND OF THE INVENTION

Analysis methods and systems of such kind are sufficiently known and are used primarily to obtain the most accurate contactless measurement possible of intraocular pressure in an eye. For example, a non-contact tonometer is used for this purpose, with the aid of which a puff of air is applied to the eye being examined, wherein an intensity of the air puff is selected such that the cornea of an eye is pressed inwards, creating a concave surface shape. The cornea briefly forms a flat surface before maximum deformation of the cornea is reached and before the cornea is indented towards the lens of the eye, this surface being called the first applanation point. After maximum deformation of the cornea has been reached and the cornea has returned to its original shape, the cornea passes through a second applanation point of the same kind. Now the intraocular pressure may be calculated by plotting a pressure of the air puff against the development of the corneal applanation over time. The measured values obtained with the non-contact tonometer are set in relation to comparison measured values that have been determined using an applanation tonometer or contact tonometer that produces relatively more accurate measurements, thus enabling a an internal eye pressure to be derived that approximates the actual intraocular pressure more closely as the result.

However, an intraocular pressure that is measured with a non-contact tonometer is not sufficiently accurate compared with a pressure measurement made with an applanation tonometer, because the measurement is distorted by the cornea, among other reasons. In order to improve the measurement accuracy, it was therefore attempted to take the influence of the cornea on the measurement into account, for example with a thickness measurement or measurement of corneal radii before conducting the measurement with a non-contact tonometer. It is also known to consider a modulus of elasticity or Young's modulus as a biomechanical property of the cornea, and to adjust the measurement in question with a corresponding calculation factor. In this context, it is assumed that the modulus of elasticity is always of the same magnitude and is thus constant for all measurements, even for different eyes. It is further assumed that the modulus of elasticity is the same for all areas of a given cornea. Consideration of a modulus of elasticity in a non-contact tonometer measurement has the disadvantage that this material characteristic or material parameter is used to characterise a tensile load, which does not occur with non-contact tonometer measurements. Moreover, a modulus of elasticity varies individually from one eye to the next and also as a function of the respective areas of the cornea within the cornea itself. Therefore, consideration of material parameters of such kind and calculation of a measurement result may still not lead to measurement results of satisfactory accuracy.

It is further known to incorporate the biomechanical properties of a cornea in a non-contact tonometer measurement during the measurement or to calculate these properties as the measurement is being conducted. For this, a puff of air is applied to the cornea, and a pump pressure is recorded continuously during the course of the measurement by a pressure sensor. A timeline of the measurement is also recorded, and first and second corneal applanation points are detected optically. An intraocular pressure may now be derived for example by determining the pressures prevailing respectively at the times of the first and second applanations, particularly since the forces necessary to deflect the cornea both inwardly and outwardly are assumed to be of the same magnitude, and thus cancel one another out. Consequently an intraocular pressure is derived from an average of the force applied for pressing the cornea inwards and outwards, in the form of the air puff.

Alternatively, it is known to determine a hysteresis point between the first and second applanation points and to derive and correct the intraocular pressure on the basis of the hysteresis measurement. In the hysteresis measurement, the first and second applanation points are detected optically and correlated with a timeline of a pressure curve of a pump, that is to say an associated time value and a pressure value is determined for each applanation point. Since the cornea is depressed inwards and the first applanation point is reached at a higher pressure than when cornea is deflected outwards again and the second applanation point is reached, this pressure difference may be used to determine the hysteresis as a material characteristic of the cornea.

The disadvantage of these measurement methods is that a movement of the cornea caused by a puff of air is subject to dynamic effects, which may distort such time/pressure measurements, particularly since the dynamic effects of the described non-contact tonometer measurements cannot be taken into account. In order to avoid such undesirable vibrations of the cornea, a speed of the air puff is minimised as far as possible to avoid distortion of the measurement result due to undesirable movement of the cornea. It is also necessary to synchronise the start of the air puff with the required time measurement. However, when a mechanical pump such as a piston pump is used to generate the air puff, it is not possible to synchronise the times with this degree of accuracy, because of the effects of inertia or friction for example, again leading to a distortion of the measurement result. Moreover, as was indicated earlier, the air puff is pressure-monitored, which means it is altered as required while the measurement is taking place. Thus the air puff is reduced or switched off after the first applanation point has been exceeded to prevent the cornea from being deflected inwards too far. However, this requires continuous monitoring of both the pump pressure and of the course thereof over time relative to the time points of the first and second applanation points, which in turn gives rise to a number of possible sources of error that might distort a measurement result. In summary, therefore, the analysis methods and systems known from the prior art, based on pressure and time measurement systems that operate independently of and parallel with one another with simultaneous detection of the applanation points, are still rather inaccurate compared with a measurement carried out using a contact tonometer.

SUMMARY OF THE INVENTION

The task underlying the present invention is therefore to suggest an ophthalmological analysis method for measuring an intraocular pressure in an eye and a system for performing such analysis, with which comparatively improved measurement accuracy may be achieved.

This task is solved according to the invention with the characteristics of an ophthalmological analysis method in that the ophthalmological analysis method measures an intraocular pressure in an eye (11) with an analysis system consisting of an actuating device with which a cornea (10) of the eye is deformed in contactless manner, wherein the actuating device causes a puff of air to be applied to the eye in such manner that the cornea is deformed, an observation system with which the deformation of the cornea is observed and recorded, wherein sectional images are created of the cornea when it is deformed and/or not deformed, and an analysis device with which the intraocular pressure is derived from the sectional images of the cornea, wherein a structural characteristic and/or material characteristic of the cornea is derived from the sectional images of the cornea in the analysis device, characterized in that a corneal stress is derived as a structural characteristic and/or material characteristic, wherein stresses are rendered visible in the material of the cornea. Additional, particularly beneficial embodiments of the invention are provided in accordance with the following subsidiary ophthalmological analysis methods.

In accordance with a second ophthalmological analysis method of the invention, the first embodiment is modified so that a material characteristic of the cornea (10) that is independent of the intraocular pressure is derived. In accordance with a third ophthalmological analysis method of the invention, the first embodiment and the second embodiment are modified so that the intraocular pressure is derived taking into account the structural and/or material characteristics of the cornea (10). In accordance with a fourth ophthalmological analysis method of the invention, the first embodiment, the second embodiment, and the third embodiment are modified so that one photoelastic representation of the cornea (10) is used as a sectional image in each case. In accordance with a fifth ophthalmological analysis method of the invention, the fourth embodiment is modified so that the structural and/or material characteristic of the cornea (10) is derived from stress lines (19) of the photoelastic representation. In accordance with a sixth ophthalmological analysis method of the invention, the first embodiment, the second embodiment, the third embodiment, the fourth embodiment, and the fifth embodiment are modified so that the analysis system is designed in the manner of a polariscope, wherein the observation system comprises an illumination system and a camera device, each of which is equipped with a polariser, wherein the eye (11) is illuminated with linearly, circularly or elliptically polarised light via the illumination device. In accordance with a seventh ophthalmological analysis method of the invention, the sixth embodiment is modified so that the eye (11) is illuminated with monochromatic or polychromatic light. In accordance with an eighth ophthalmological analysis method of the invention, the sixth embodiment and the seventh embodiment are modified so that a polarisation direction is rotated relative to the sectional image. In accordance with a ninth ophthalmological analysis method of the invention, the first embodiment, the second embodiment, the third embodiment, the fourth embodiment, the fifth embodiment, the sixth embodiment, the seventh embodiment, and the eighth embodiment are modified so that a stiffness of the cornea (10) is derived as a material characteristic, wherein the intraocular pressure is derived taking into account the material characteristics of the cornea. In accordance with a tenth ophthalmological analysis method of the invention, the first embodiment, the second embodiment, the third embodiment, the fourth embodiment, the fifth embodiment, the sixth embodiment, the seventh embodiment, the eighth embodiment, and the ninth embodiment are modified so that a speed of the movement of the cornea (10) is measured for the purpose of deriving the material characteristic. In accordance with an eleventh ophthalmological analysis method of the invention, the first embodiment, the second embodiment, the third embodiment, the fourth embodiment, the fifth embodiment, the sixth embodiment, the seventh embodiment, the eighth embodiment, the ninth embodiment, and the tenth embodiment are modified so that a maximum deformation of the cornea (10) is derived from the sectional images of the cornea for the purpose of deriving the material characteristic. In accordance with a twelfth ophthalmological analysis method of the invention, the first embodiment, the second embodiment, the third embodiment, the fourth embodiment, the fifth embodiment, the sixth embodiment, the seventh embodiment, the eighth embodiment, the ninth embodiment, the tenth embodiment, and the eleventh embodiment are modified so that an amplitude of the deformation of the cornea (10) is derived from the sectional images of the cornea for the purpose of deriving the material characteristic. In accordance with a thirteenth ophthalmological analysis method of the invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, and the twelfth embodiment are modified so that a curvature of the cornea (10) with and/or without deformation is derived from the sectional images of the cornea for the purpose of deriving the structural and/or material characteristic. In accordance with a fourteenth ophthalmological analysis method of the invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, and the thirteenth embodiment are modified so that a parameter of a flat applanation area is measured when an applanation point of the cornea (10) is reached for the purpose of deriving the material characteristic. In accordance with a fifteenth ophthalmological analysis method of the invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, the thirteenth embodiment, and the fourteenth embodiment are modified so that a shear modulus (G) of the cornea (10) is derived as a material characteristic. In accordance with a sixteenth ophthalmological analysis method of the invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, the thirteenth embodiment, the fourteenth embodiment, and the fifteenth embodiment are modified so that a scattering of light by the cornea (10) is derived from a sectional image of the cornea, wherein an elasticity of the cornea is derived from the light scattering of a single sectional image. In accordance with a seventeenth ophthalmological analysis method of the invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, the thirteenth embodiment, the fourteenth embodiment, the fifteenth embodiment, and the sixteenth embodiment are modified so that structural and/or material characteristics that differ from each other are allocated to different areas of the cornea (10) in each case. In accordance with a eighteenth ophthalmological analysis method of the invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, the thirteenth embodiment, the fourteenth embodiment, the fifteenth embodiment, the sixteenth embodiment, and the seventeenth embodiment are modified so that the observation system comprises a camera and an illumination device in a Scheimpflug arrangement, wherein the sectional images are taken with the camera.

This task is also solved according to the invention with the characteristics of an ophthalmological analysis system in that the ophthalmological analysis system for measuring an intraocular pressure in an eye (11), comprises an actuating device with which a cornea (10) of the eye can be deformed in contactless manner, wherein the actuating device causes a puff of air to be applied to the eye in such manner that the cornea is deformed, an observation system with which the deformation of the cornea can be observed and recorded, wherein sectional images of the cornea when it is deformed and/or not deformed can be created with the observation system, and an analysis device with which the intraocular pressure can be derived from the sectional images of the cornea, wherein a structural characteristic and/or a material characteristic of the cornea can be derived from the sectional images of the cornea in the analysis device, characterized in that a stress of the cornea is derived as a structural and/or material characteristic, wherein the stresses in the corneal material are rendered visible.

In the ophthalmological analysis method according to the invention for measuring an intraocular pressure in an eye with an analysis system, generally, the analysis system includes an actuating device with which the cornea of the eye is deformed in contactless manner, wherein the actuating device causes a puff of air to be applied to the eye in such manner that the cornea is deformed, an observation system with which the deformation of the cornea is observed and recorded, wherein sectional images of the cornea when it is deformed and/or not deformed are created with the observation system, and an analysis device with which the intraocular pressure is derived from the sectional images of the cornea, wherein a structural characteristic and/or a material characteristic of the cornea is derived from the sectional images of the cornea in the analysis device, wherein a corneal stress is derived as a structural and/or a material characteristic, wherein stresses in the material of the material are rendered visible.

In the present context, a material characteristic is defined as a characteristic that is intrinsic to the material and is unaffected by external influences. A structural characteristic is a characteristic that is affected by external influences in the material, or even by the shape of the material. According to the invention, it provision is made to render corneal stresses visible by capturing sectional images. In this context, a distinction may be made between stresses that are independent of an intraocular pressure and those that do depend on an intraocular pressure and are created in the corneal material due to the deformation of the cornea. This distinction is made possible by the capture of sectional images that capture the stresses in the cornea before deformation and the subsequent stresses in the deformed cornea and render them visible. The intraocular pressure may be corrected taking these stresses into account depending on the type, magnitude, direction and distribution of the stresses in the sectional images of the cornea.

The material characteristic may also be derived as a material characteristic of the cornea independent of intraocular pressure. In this way, the intraocular pressure and the corneal material characteristic may then be determined particularly accurately separately from one another as independent material characteristics describing the cornea.

Moreover, the intraocular pressure may also be derived with consideration for the structural and/or material characteristics of the cornea. In particular, it may be possible to correct the intraocular pressure by comparing a ratio between the stresses in the cornea before and during deformation, at a defined point or position of the deformed cornea. In a further step of the method, it may be provided that the visibly represented stresses may be compared with visibly represented stresses stored in a database for the purpose of correcting the intraocular pressure. In this way, an objective intraocular pressure or also a corresponding correction value is then known for the values stored in the database, so that the objective intraocular pressure of the eye being measured may be derived with consideration for the corneal stresses.

One photoelastic representation of the cornea may be used as a sectional image in each case. A photoelastic representation makes it easy to display the distribution of stresses in translucent bodies, and it is easy to display the respective distribution and magnitude of mechanical stresses in all parts of the cornea, or even in other translucent areas of the eye, and to evaluate them via image processing. In particular, stresses that occur in the plane of the sectional image may be rendered visible. Stresses that extend transversely to the plane of the sectional image are then ignored, and it is not essential to take these into account for the purpose of correcting the intraocular pressure.

The further material characteristic of the cornea may be derived particularly easily from stress lines on the photoelastic imaging. The stress lines are very clearly visible, and this also makes it easy to distinguish between the structural and the material characteristic of the cornea. A distinction may be made between isochromates or isoclines, isochromates being stress lines that have a constant principal stress differential and isoclines representing stress trajectories of the cornea under a given load. In this way, on the basis of a large number of sectional images obtained during a corneal deformation it is possible to distinguish between stress lines that are changed by the load on the cornea caused by the air puff and stress lines that are present in the cornea due to the shape of the cornea itself and which do not change significantly relative to the cornea.

The analysis system may be configured in the manner of a polariscope, and the observation system may then comprise an illumination device and a camera device, each of which is equipped with a polariser, in which case the eye may be illuminated with linearly, circularly or elliptically polarised light via the illumination device. For example, it may then be sufficient to provide an appropriate polarisation filter on the illumination device and a polarisation filter on the camera device in order to render stresses in the corneal material visible. The various types of polarised light may then be used to create various effects and achieve suitable visualisation. For example, isoclines are not visible when circularly polarised light is used.

In this respect, it is also possible to illuminate the eye with monochromatic or polychromatic light. When monochromatic light is used, dark and light stripes appear in the sectional image of the cornea, the arrangement of which enables conclusions to be drawn regarding the mechanical stresses of the cornea. Polychromatic light further enables colour representation of the stripes and stress lines.

Alternatively, a polarisation direction may also be rotated relative to the sectional image so that the representation may be adapted.

A stiffness of the cornea may be derived as a further material characteristic, wherein the intraocular pressure may then be derived with consideration for the material characteristics of the cornea. The concept of stiffness in this context is explicitly not to be understood as a modulus of elasticity or a Young's modulus, but rather as a material characteristic that is characterized by or responds to a pressure load acting on the eye, that is to say the loading condition that actually exists at the time of a tonometer measurement. Stiffness is thus a direction-dependent parameter of the corneal material. Stiffness is also determined by the corneal material itself and not by other, external influences. Intrinsic stresses that affect the stiffness of the cornea may also operate within the corneal material.

Intraocular pressure and stiffness of the cornea may each be determined separately from each other as independent further material characteristics the describe the cornea. Thus, according to a conventional tonometric method a first intraocular pressure may be determined during a single measurement by applying a puff of air. At the same time, the stiffness of the cornea may be derived from the deformation of the cornea that is recorded by the observation system during the deformation. Since the stiffness of the cornea significantly influences a deformation behaviour of the cornea and the measurement of the first intraocular pressure of the eye, allowance may be made for the influence of the cornea on the measurement of the first intraocular pressure. Thus, the previously measured first intraocular pressure may be corrected by the influence of the cornea on the measurement so that an objective intraocular pressure is derived as a result of the measurement. In these circumstances, stiffness of the cornea is essentially an approximately a linear function of the first measured, subjective intraocular pressure of the eye and a measured maximum amplitude of the deformation of the cornea. On a graph of the function of the stiffness, for example, the subjective intraocular pressure may be plotted on a vertical axis, and the maximum amplitude of deformation on a horizontal axis, so that stiffness then has the form of an essentially straight line with a negative gradient. The changes in the measurement values essentially cause a parallel shift in the straight line depending on the measurement values for the horizontal and vertical axes, from which differing stiffnesses may result in each case. The objective intraocular pressure may be derived from the measured stiffness or it may be deduced from the linear stiffness plot from an intersection of the value for subjective intraocular pressure and the value for maximum amplitude with the linear plot for stiffness. During measurement, stiffness of the cornea may always be recalculated as a further material characteristic for each measurement, that is to say it is not assumed, as is the case in the prior art, that the material characteristic is a constant for any given eye.

It may also be particularly advantageous if a series or plurality of sectional images of the cornea is captured during the measurement or cornea deformation process. It this way, it becomes possible to monitor a deformation of the cornea in close detail, and to derive the corresponding material characteristic or an objective intraocular pressure from the progress of the deformation by processing the sectional images.

A period of time between the start and end of the deformation of the cornea may also be measured to enable a further material characteristic to be derived. In particular, it then becomes possible to assign all of the sectional images recorded to a given point of time in the measurement, so that the chronological sequence of the deformation may be tracked. In particular, a point in time of the first and second applanations of the cornea and therewith also a temporal offset between them may be determined precisely. Thus, the calculation of this time period may also be sufficient for determining the pertinent material characteristic. In addition, a time period of the entire deformation of the cornea may be used for deriving the material characteristic.

A speed of the movement of the cornea may be measured to derive a further material characteristic. In particular, if the temporal progression of a deformation of the cornea is known, a dynamic of the deformation may also be examined, so that particular dynamic effects may be evaluated with respect to the respective material characteristic. For example, post-oscillation of the cornea after an air puff no longer has the effect of distorting the measurement result if the post-oscillation is taken into account during the measurement. Moreover, a speed of an air puff relative to otherwise undesirable dynamic effects is also freely selectable for a measurement. It is also possible to draw conclusions about an indentation depth or maximum amplitude on the basis of the measured speed, since a functional relationship exists between these parameters.

In order to derive the structural and/or additional material characteristic more accurately still, a maximum deformation of the cornea may be derived from the sectional images of the cornea for deriving the structural and/or additional material characteristic. Accordingly, a maximum indentation depth of the cornea may be determined from the sectional images of the cornea, in which case a supplementary point in time of maximum corneal deformation may be established at least relative to one of the applanation points.

The structural and/or material characteristic of the cornea may be determined even more accurately if an amplitude of the corneal deformation is derived from the sectional images of the cornea. In this way, it is easy to track the precise geometrical progression of the deformation. This means that for any point in time of the deformation, the precise geometrical contour of the deformation subsisting at that time may be recorded, so that the geometrical progression of the deformation may be captured in the manner of a film of the deformation. For example, it is thus possible to capture a clear record even of post-oscillation of the cornea after it springs back, that is to say after the second applanation point.

In order to derive the structural and/or material characteristic more accurately still, a curvature of the cornea with and/or without deformation may be derived from the sectional images of the cornea. Since the sectional images of the cornea also describe a geometry thereof, particularly before the air puff is applied, the geometry of the cornea may be included in the calculation of the objective intraocular pressure in conjunction with the respective material characteristic of the cornea. This means that the radii of curvature or a curvature of the cornea on an outer and/or inner corneal surface may be derived from the sectional images by image processing. In this context, the radii of curvature may be included as a correction factor when measuring the cornea without deformation and, for example, the thickness of the cornea may be used as a correction factor when measuring with cornea with deformation, thus serving as an indicator for the material characteristic.

Optionally, a parameter of a flat applanation area when a corneal applanation point is reached may also be measured in order to derive a further material characteristic. For example, a parameter of the applanation area or the diameter thereof and/or its shape may be considered as an indicator of the stiffness of the cornea. The corneal radii adjacent to the respective applanation area may also be used as an indicator.

In this context, a diameter $d_1$ of a first applanation area of the cornea and a diameter $d_n$ of a deformation area of the cornea differing from the first applanation area of the cornea may also be derived. When the cornea is deformed by the air puff, the cornea may be completely flattened, in which case a first applanation area is formed having diameter $d_1$. The applanation area is then essentially flat and in the region of an applanation plane lies orthogonally to an optical axis of the eye or a device axis of an analysis system. While the cornea is deformed, a concave depression that differs significantly from the first applanation area is formed in the cornea. If the deformation area of the depression differing from the first applanation area is compared with the first applanation area, the further material characteristic of the cornea may be defined, since the formation of the deformation area is also dependent on the further material characteristic. In this case, a reference scale for the deviation may be the first applanation area or diameter $d_1$ of the first applanation area. If the comparison is made with diameter $d_n$ of the corneal deformation area, this comparison may be made particularly easily. Diameter $d_n$ may be determined very easily, particularly in the case of a deformation movement of the cornea after passing the first applanation area or a first applanation point, since the deformation area then assumes a concave shape. The deformation area or diameter $d_n$ in a specified time period of the deformation relative to the first applanation area, or even another measurable point or position of the cornea during the deformation may be used to define the deviating deformation area of the cornea. The calculated deviation and the relative values of the pertinent diameters may also be stored in a database and compared. Thus, an objective intraocular pressure or also a corresponding correction value may be known for the values stored in the database, so that the objective intraocular pressure of the eye being measured may be derived taking into account the geometrically defined material characteristic of the cornea.

In order to derive the further material characteristic, a diameter $d_2$ of a deformation area of the cornea may be determined for a maximum deformation of the cornea in the direction of a visual axis or a device axis. The maximum corneal deformation may be determined from a series of sectional images of the deformed cornea. In this way, it is possible to define a point in time of the definition or a geometry of the cornea for each measurement, which may be used as a reference for comparison with the first applanation area of the cornea. Diameter $d_2$ may then also be determined simply by defining it as a distance between two opposite points in a longitudinal sectional plane of the cornea when the cornea is in the state of maximum deformation, wherein each of the points represents the points closest to the analysis system. These points may be taken from a sectional image and accordingly represent diameter $d_2$ of the maximum corneal deformation.

In order to derive the further material characteristic, a ratio may be determined between diameter $d_1$ of the first applanation area of the cornea and a diameter $d_3$ of a second applanation area of the cornea. During deformation of the cornea by the air puff the cornea is depressed inwards, forming the first applanation area, until it reaches a maximum deformation of the cornea with a concave depression, and the cornea subsequently springs back, forming the second, largely flat applanation area until the cornea regains its original shape. The second applanation area thus represents an easily recognisable geometric reference point in the sectional images, which may be used for defining the material characteristic by comparing with the first applanation area. A material characteristic of the cornea may be defined or determined particularly by any differences in the diameters of the applanation areas. The corneal radii adjacent to the respective applanation area may also be used as a further indicator.

A shear modulus (G) of the cornea may be derived as a further material characteristic. A shear modulus may be used as a linear material characteristic to serve as a particularly simplified indicator of corneal stiffness, particularly since a linear material behaviour of such kind may be interpreted with little effort by the analysis device.

In order to consider elasticity as a further material characteristic of the cornea for measurement as well as stiffness, the light scattering effect of the cornea may be derived from a sectional image of the cornea, wherein the elasticity of the cornea is derived as a material characteristic from the light scattering effect in a single sectional image. Visible clouding of the cornea may serve as an indicator of material aging of the cornea, and conclusions regarding the elasticity of the cornea may be drawn from its age. Accordingly, if a cornea presents advanced cloudiness and thus also increased light scattering, it is relatively less elastic than a cornea in which light is less scattered. In this case, the elasticity of the cornea may be treated as an individual modulus of elasticity of the eye being measured.

The measurement may be further improved by assigning structural and/or material characteristics that differ from each other to different areas of the cornea. Thus, assuming that the cornea is of uniform thickness the material characteristics may vary or differ from each other in different regions of a cross-section of the cornea or with reference to a surface area of the cornea.

In an advantageous embodiment of the analysis method, the observation system may comprise a camera and an illumination device in a Scheimpflug arrangement, wherein the sectional images may then be taken with the camera. This means that the camera may be positioned relatively close to an optical axis of a slit lighting device for illuminating the eye in a Scheimpflug arrangement, so that an illuminated sectional image of the eye may be taken with the camera. A camera may also be used as a high-speed camera, for example, capable of capturing at least 4000 images per second. The optical axis of the slit lighting device may also coincide or be congruent with a visual axis of the eye. An effective direction of the air puff may then preferably be coaxial with the optical axis of the slit lighting device.

The ophthalmological analysis system according to the invention for measuring an intraocular pressure in an eye, generally, comprises an actuating device with which a cornea of an eye may be deformed in contactless manner, wherein a puff of air may be applied to the eye via the actuating device to cause deformation of the cornea, an observation system with which the deformation of the cornea may be observed and recorded, wherein sectional images are created of the cornea when it is deformed and/or not deformed, and an analysis device with which the intraocular pressure may be derived from the sectional images of the cornea, wherein a structural characteristic and/or a material characteristic of the cornea that is independent of the intraocular pressure is derived from the sectional images of the cornea in the analysis device, wherein a stress of the cornea is derived as a structural characteristic and/or material characteristic, wherein stresses in the corneal material are made visible, wherein the intraocular pressure is derived taking into account the structural and/or material characteristics of the cornea.

BRIEF DESCRIPTION OF THE INVENTION

In the following, a preferred embodiment of the invention will be explained in greater detail with reference to the accompanying drawing.

Figure 2:
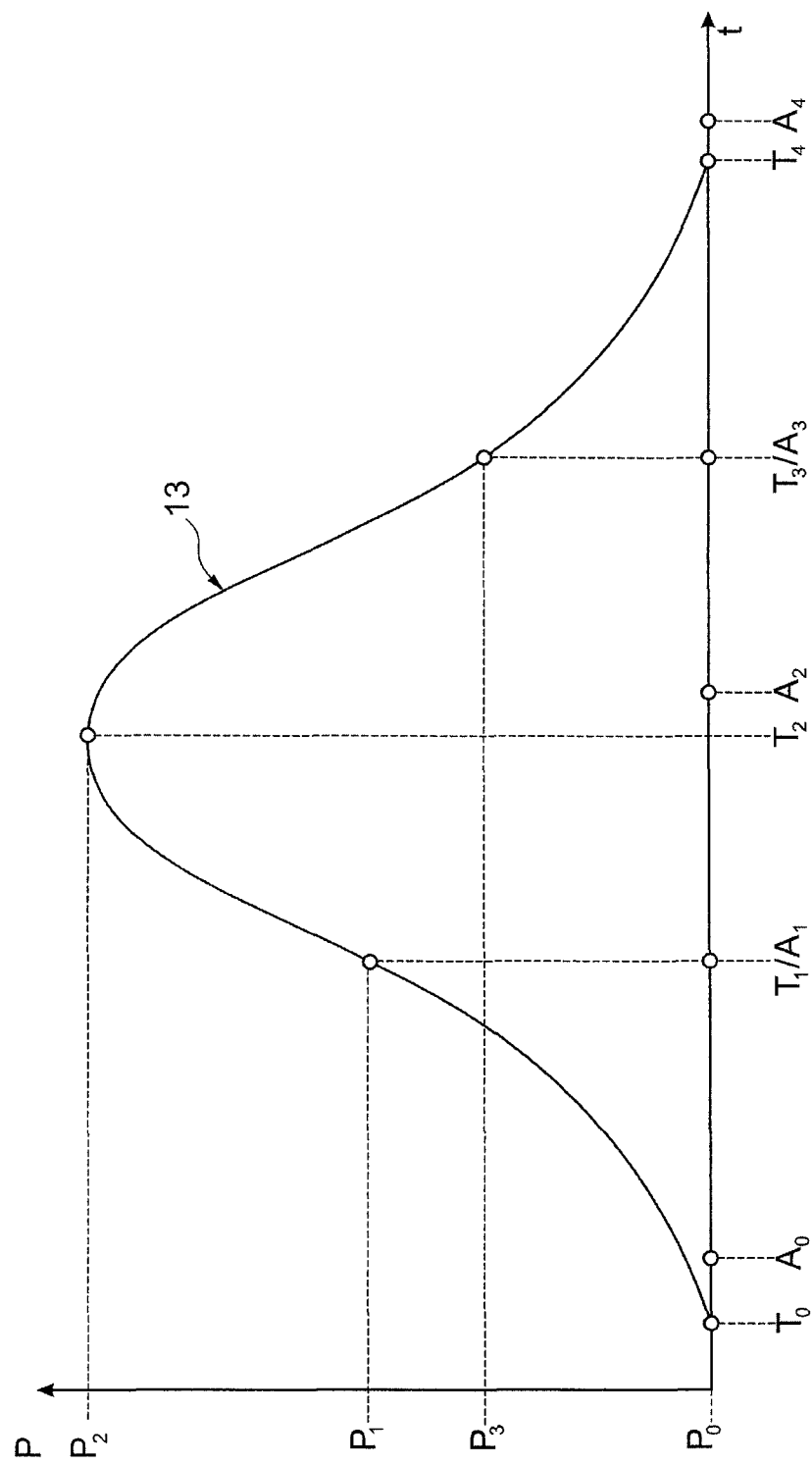
Figure 3:
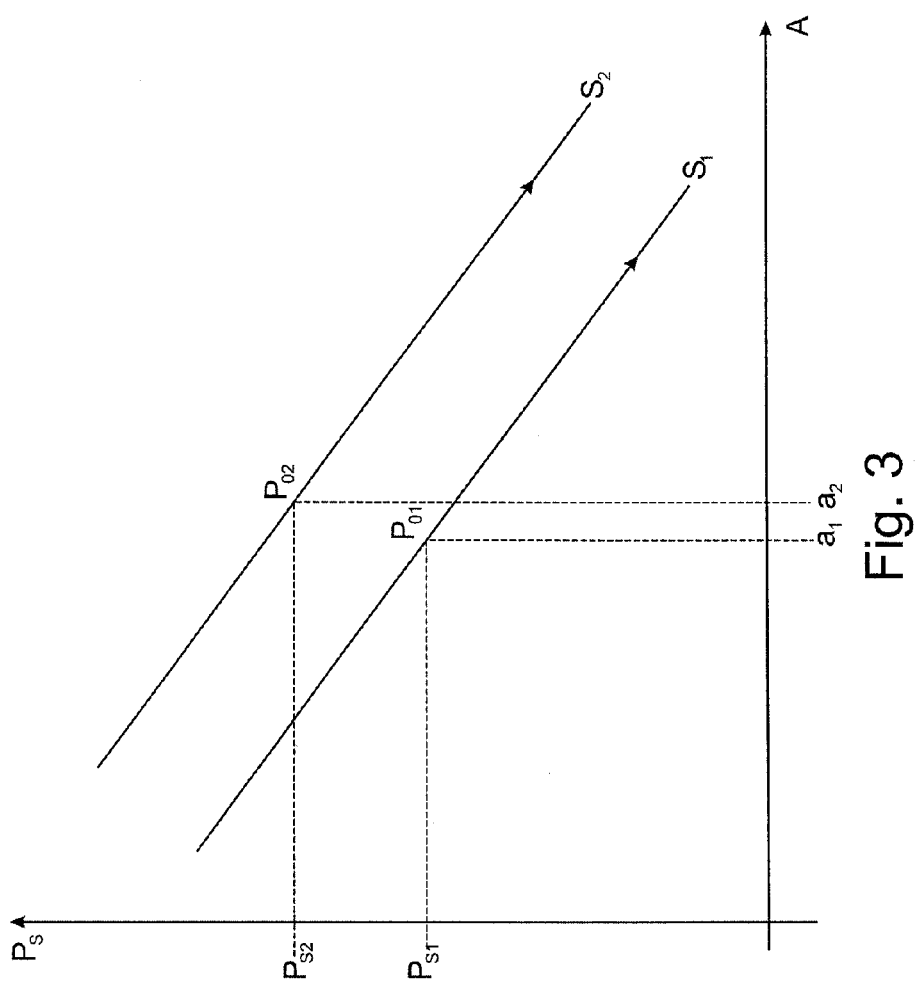
Figure 4A:
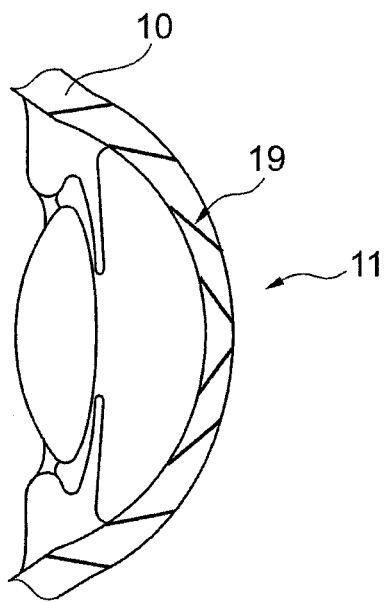
Figure 4B:
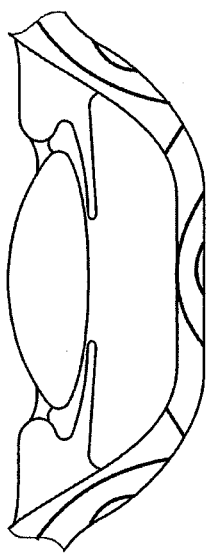

In the drawing:

FIGS. 1a to 1e: show a longitudinal cross-section of a deformation of a cornea of an eye during a measurement;

FIG. 2: is a graph representation of the pump pressure and time during a measurement;

FIG. 3: is a graph representation of the measured intraocular pressure and deformation of a cornea;

FIGS. 4a to 4b: are a visible representation of stresses in the corneal material of the eye.

DETAILED DESCRIPTION OF THE INVENTION

FIGS. 1a to 1e show selected deformation states of a cornea 10 of an eye 11 during a single measurement of an intraocular pressure via an analysis system, not shown here. Each of the drawings is a longitudinal cross-section along an optical axis 12 of eye 11. FIG. 2 is a graph representation with a time t plotted on the horizontal axis and a pump pressure p on the vertical axis. The plot of the pump pressure has the form of a symmetrical bell curve 13, beginning with pump pressure $P_0$ at a start point $T_0$ of the pump, rising to a maximum pump pressure $P_2$ at time $T_2$, and then falling to pump pressure $P_0$ again at an end time $T_4$, which curve is unaffected by the use of an observation system, not shown here, and a Scheimpflug camera with a slit lighting device. The air puff directed at cornea 10 when the pump starts at $T_0$ causes a first deformation of cornea 10 immediately after time $A_0$, which deformation is recordable with the observation system. FIG. 1a represents the shape of cornea 10 at time $A_0$, before it is deformed. As the pump pressure increases, at time $A_1$ cornea is fully applanated as shown in FIG. 1b, wherein an applanation area 14 having diameter $d_1$ is formed, this area being essentially flat and lying in an applanation plane 15. At this point the cornea is offset or indented with respect to apex 16 of cornea 10 by a dimension $X_1$. Optionally, but not necessarily, a pump pressure $P_1$ for corresponding time $T_1$ may be calculated for this first applanation point at time $A_1$. After pump pressure $P_2$ is reached, cornea 10 is in the condition of maximum deformation at time $A_2$, as represented in FIG. 1c. In this condition, a point 17 defining a maximum deformation is offset from apex 16 of cornea 10 by a dimension $X_2$. In this case, this therefore represents a maximum deflection of a deformation amplitude. At this maximum deformation amplitude, a diameter $d_2$ of a concave deformation area 18 is formed and recorded. Diameter $d_2$ is defined by a distance between two opposite points of a longitudinal sectional plane of cornea 10, wherein each of the points represents the points of cornea 10 closest to the analysis system. This is followed by a return movement or oscillation of cornea 10, wherein the second applanation point is reached at time $A_3$, as shown in FIG. 1d. At this point, a diameter $d_3$, and a distance $X_3$ are also recorded. It is also optionally possible to determine a pump pressure $P_3$. for matching time point $T_3$. After the pump pressure has fallen back to the original value $P_0$ at time $T_4$, cornea 10 also regains its original condition, as shown in FIG. 1e, at time $A_4$. The deformation states of cornea 10, which are characterized respectively by times $A_0$ to $A_4$, are calculated according to the preceding description of a single measurement of an intraocular pressure of an eye as shown in FIGS. 1a to 1e. In this process, in particular time offsets of the associated time points $A_0$ to $A_4$ and dimensions or indentation depths $X_1$, $X_2$ and $X_3$ are recorded without reference to a pump pressure p, and a stiffness of cornea 10 is derived from these parameters. A measured intraocular pressure is than corrected with a value determined by the stiffness of the cornea, such that an objective intraocular pressure is output as the result of the measurement.

FIG. 3 shows a graph representation with a subjective, measured intraocular pressure on the vertical axis plotted against a deflection amplitude of a maximum deformation of cornea 10 on the horizontal axis. For example, a subjective intraocular pressure on $P_{s1}$ and an amplitude $a_1$, which corresponds to a distance $X_2$ yields a stiffness $S_1$ as an essentially linear function with a downward gradient. However, $S_1$ may also deviate from a linear function and have the form of a line with a relatively large radius of curvature. An objective intraocular pressure $P_{o1}$ may be read off as a variable from the straight line defined by stiffness $S_1$. Similarly, a pressure $P_{s2}$ and a deflection $a_2$ also yields parallel shift of the straight line with a stiffness $S_2$ and a further objective intraocular pressure $P_{o2}$ may also be derived from this. Alternatively, diameters $d_1$ and $d_2$ may also be used in the graph instead of amplitudes $a_1$ and $a_2$ and used similarly.

FIGS. 4a to 4b show the deformation states of cornea 10 of eye 11 in similar manner to FIGS. 1a and 1b. Unlike these, however, FIGS. 4a to 4b show the stresses in the corneal material. For example stress lines 19 in the material of cornea 10 are displayed particularly clearly, representing the principal stresses along and transversely to optical axis 12. FIG. 4a thus shows stresses in eye 11 with cornea 10 in a resting position, and FIG. 4b shows stresses in eye 11 with a deformed cornea 10, wherein these stresses differ from the stresses in the resting condition. A comparison of stress based on stress lines 19 thus enables a structural and/or material characteristic of the cornea to be defined, which may be used to correct a measured intraocular pressure and thus also to derive an objective intraocular pressure.

The invention claimed is:
1. An ophthalmological analysis method for measuring an intraocular pressure in an eye with an analysis system including an actuating device with which a cornea of the eye is deformed in contactless manner, the method comprising the following steps:
    (a) applying a puff of air to an eye with an actuating device in such manner that a cornea of the eye is deformed;
    (b) observing and recording a deformation of the cornea with an observation system;
    (c) creating sectional images of the cornea when the cornea is deformed or is not deformed according to step (a) with the observation system; and

(d) deriving an intraocular pressure from the sectional images of the cornea with an analysis device,
wherein a structural characteristic or a material characteristic or the structural characteristic and the material characteristic of the cornea are derived from the sectional images of the cornea in the analysis device, wherein a corneal stress is derived as the structural characteristic or the material characteristic or the structural characteristic and the material characteristic, wherein the stress is rendered visible in the material of the cornea.

2. The analysis method as recited in claim 1, wherein the material characteristic of the cornea is independent of the intraocular pressure.

3. The analysis method as recited in claim 1, wherein the intraocular pressure is derived taking into account the structural characteristic or the material characteristic or the structural characteristic and the material characteristic of the cornea.

4. The analysis method as recited in claim 1, wherein one photoelastic representation of the cornea is used as each sectional image.

5. The analysis method as recited in claim 4, wherein the structural characteristic or the material characteristic or the structural characteristic and the material characteristics of the cornea is derived from stress lines of the photoelastic representation.

6. The analysis method as recited in claim 1, wherein the analysis system is designed in the manner of a polariscope, wherein the observation system comprises an illumination device and a camera device, wherein both the illumination device and the camera device are equipped with a polarizer, and wherein the eye is illuminated with linearly, circularly or elliptically polarized light via the illumination device.

7. The analysis method as recited in claim 6, wherein the eye is illuminated with monochromatic or polychromatic light.

8. The analysis method as recited in claim 6, wherein a polarisation direction is rotated relative to the sectional image.

9. The analysis method as recited in claim 1, wherein the material charateristic is derived from a stiffness of the cornea characteristic, and wherein the intraocular pressure is derived taking into account the material characteristic of the cornea.

10. The analysis method as recited in claim 1, wherein the speed of the movement of the cornea is measured, and wherein the material characteristic is derived from the speed of the movement of the cornea.

11. The analysis method as recited in claim 1,
wherein the material characteristic is derived from a maximum deformation of the cornea, and wherein the maximum deformation of the cornea is derived from the sectional images of the cornea.

12. The analysis method as recited in claim 1, wherein the material characteristic is derived from an amplitude of the deformation of the cornea, and wherein the amplitude of the deformation of the cornea is derived from the sectional images of the cornea.

13. The analysis method as recited in claim 1, wherein the characteristic of the material characteristic or the structural characteristic and the material characteristic is derived from a curvature of the cornea with deformation or a curvature of the cornea without deformation or a curvature of the cornea with deformation and a curvature of the cornea without deformation, and wherein the curvature of the cornea with deformation or the curvature of the cornea without deformation or the curvature of the cornea with deformation and the curvature of the cornea without deformation are derived from the sectional images of the cornea.

14. The analysis method as recited in claim 1, wherein a parameter of a flat applanation area is measured when an applanation point of the cornea is reached and wherein the material characteristic is derived from the parameter of the flat applanation area.

15. The analysis method as recited in claim 1, wherein the mqaterial characteristic is derived from a shear modulus of the cornea.

16. The analysis method as recited in claim 1, wherein a scattering of light by the cornea is derived from each sectional image of the cornea, and wherein an elasticity of the cornea is derived from the light scattering of each sectional image.

17. The analysis method as recited in claim 1,
wherein structural characteristics or material characteristics or structural characteristics and material characterisitics that differ from each other are each allocated to different areas of the cornea.

18. The analysis method as recited in claim 1, wherein the observation system comprises a camera and an illumination device in a Scheimpflug arrangement, and wherein the sectional images are taken with the camera.

19. An ophthalmological analysis system for measuring an intraocular pressure in an eye, comprising:
(i) an actuating device that can deform a cornea of an eye in contactless manner, wherein the actuating device applies a puff of air applied the eye in such manner that the cornea is deformed;
(ii) an observation system that observes and records a deformation of the cornea, wherein the observation system creates sectional images of the cornea when the cornea is deformed or when the cornea is not deformed or when the cornea is deformed and when the cornea is not deformed; and
(iii) an analysis device that derives an intraocular pressure from the sectional images of the cornea,
wherein a structural characteristic or a material characteristic or a structural characteristic and a material characteristic of the cornea can be derived from the sectional images of the cornea in the analysis device, wherein a corneal stress is derived as the structural characteristic or the material characteristic or the structural characteristic and the material characteristic, wherein the stress is rendered visible in the material of the cornea.

20. An ophthalmological analysis method for measuring an intraocular pressure in an eye with an analysis system including an actuating device with which a cornea of the eye is deformed in contactless manner, the method comprising the following steps:
(a) applying a puff of air to an eye with an actuating device in such manner that a cornea of the eye is deformed, wherein the actuating device includes a pump;
(b) observing and recording a deformation of the cornea with an observation system, wherein the observation system comprises an illumination device and a camera device, wherein both the illumination device and the camera device are equipped with a polarizer, and wherein the illumination device is a slit lighting device and the camera device is a Scheimpflug camera;
(c) creating sectional images of the cornea when the cornea is deformed or is not deformed according to step (a) with the observation system; and (d) deriving an intraocular pressure from the sectional images of the cornea with an analysis system, wherein the analysis system is designed in the manner of a polariscope, wherein a structural characteristic or a material characteristic or the structural characteristic and the material characteristic of the cornea are derived from the sectional images of the cornea in the analysis device, wherein a corneal stress is derived as the structural characteristic or the material characteristic or the structural characteristic and the material characteristic, wherein the stress is rendered visible in the material of the cornea.

* * * * *